US006919310B2

(12) United States Patent
Clemens

(10) Patent No.: US 6,919,310 B2
(45) Date of Patent: *Jul. 19, 2005

(54) METHOD OF TREATING THE SYNDROME OF CORONARY HEART DISEASE RISK FACTORS IN HUMANS

(75) Inventor: Anton H. Clemens, Madison, WI (US)

(73) Assignee: CPD, LLC, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/377,838

(22) Filed: Mar. 3, 2003

(65) Prior Publication Data

US 2003/0149076 A1 Aug. 7, 2003

Related U.S. Application Data

(63) Continuation-in-part of application No. 09/878,834, filed on Jun. 11, 2001, now Pat. No. 6,528,520, which is a continuation-in-part of application No. 09/639,061, filed on Aug. 15, 2000, now Pat. No. 6,262,062.

(51) Int. Cl.$^7$ .................. A61K 38/00; A61K 31/44; A61K 31/445; A61K 31/175; A61K 31/135

(52) U.S. Cl. .................. 514/2; 514/282; 514/331; 514/592; 514/647

(58) Field of Search .................. 514/282, 2, 331, 514/592, 647

(56) References Cited

U.S. PATENT DOCUMENTS

| | | |
|---|---|---|
| 4,055,175 A | 10/1977 | Clemens et al. |
| 4,217,353 A | 8/1980 | Smith, Jr. |
| 4,272,540 A | 6/1981 | Razdan et al. |
| 4,451,470 A | 5/1984 | Ganti |
| 4,478,840 A | 10/1984 | Smith, Jr. |
| 4,511,570 A | 4/1985 | Tuttle |
| 4,619,936 A | 10/1986 | Balkanyi et al. |
| 4,760,069 A | 7/1988 | Rzeszotarski et al. |
| 4,857,533 A | 8/1989 | Sherman et al. |
| 4,863,928 A | 9/1989 | Atkinson et al. |
| 4,877,791 A | 10/1989 | Sherman |
| 4,880,813 A | 11/1989 | Frost |
| 4,882,335 A | 11/1989 | Sinclair |
| 4,888,346 A | 12/1989 | Bihari et al. |
| 4,994,466 A | 2/1991 | Sherman |
| 5,013,739 A | 5/1991 | Bihari et al. |
| 5,086,058 A | 2/1992 | Sinclair et al. |
| 5,356,900 A | 10/1994 | Bihari et al. |
| 5,468,755 A | 11/1995 | Cincotta et al. |
| 5,578,645 A | 11/1996 | Askanazi et al. |
| 5,626,860 A | 5/1997 | Cincotta et al. |
| 5,727,570 A | 3/1998 | Clemens |
| 5,830,895 A | 11/1998 | Cincotta et al. |
| 5,863,555 A | 1/1999 | Heiber et al. |
| 5,878,750 A | 3/1999 | Clemens |
| 6,026,817 A | 2/2000 | Clemens |
| 6,159,500 A | 12/2000 | Demopoulos et al. |
| 6,190,691 B1 | 2/2001 | Mak |
| 6,262,062 B1 | 7/2001 | Clemens |
| 6,528,520 B2 * | 3/2003 | Clemens .................. 514/282 |
| 2003/0036546 A1 | 2/2003 | Clemens |
| 2003/0105121 A1 | 6/2003 | Bihari |

FOREIGN PATENT DOCUMENTS

| | | |
|---|---|---|
| EP | 0 078 434 | 5/1983 |
| EP | 0 541 192 | 5/1993 |
| GB | 2045758 | 11/1980 |
| WO | WO 97/18781 | 5/1997 |
| WO | WO 97/35608 | 10/1997 |
| WO | WO 99/04795 | 2/1999 |
| WO | WO 99/59997 | 11/1999 |
| WO | WO 02/100390 | 12/2002 |
| WO | WO 03/026635 | 4/2003 |

OTHER PUBLICATIONS

Cole, Evaluation of Chronic Opioid Receptor Antagonist Effects Upon Weight and Intake Measures in Lean and Obese Zucker Rats, Peptides, vol. 18, No. 8, 1997 pp. 1201–1207.

Shaw, The Effect of the Opiod Antagonist LY255582 on Body Weight of the Obese Zucker Rat, International Journal of Obesity, vol. 15, No. 6, Jun. 1991, pp. 387–395.

Givens, et al., Reduction of Hyperinsulinemia and Insulin Resistance by Opiate Receptor Blockade in the Polycystic Ovary Syndrome with Acanthosis Nigricans, Journal of Clinical Endocrinology and Metabolism, New York NY, vol. 64, No. 2, Feb. 1987, pp. 377–382.

Wexler, et al., Anti–Opiate (Naloxone) Suppression of Cushingoid Degenerative Changes in Obese/SHR, International Journal of Obesity, Newman Publishing London, vol. 9, No. 2, 1985 pp. 77–91.

McIntosh, et al., The Effects of Opioid Receptor Selective Antagonists and Agonists Following Coronary Artery Occlusion in Anaesthetised Rats, Journal of Molecular and Cellular Cardiology, vol. 22, No. Suppl 3, Oct. 1990 (1990–10) p. S72.

Pearce, et al., Effects of X–Opioid and AVP–V1 Recetor Antagonists on the Compensatory Hemodynamic Responses of Anesthetized Rats Following Acute Hemorrhage, Canadian Journal of Physiology and Pharmacology Ottawa, Ont, CA, vol. 70, No. 5, 1992, pp. A18–A19.

(Continued)

Primary Examiner—Raymond J. Henley, III
(74) Attorney, Agent, or Firm—Michael Best & Friedrich LLP

(57) ABSTRACT

The invention provides an improved method of treating a human suffering from one or more conditions included within the Coronary Heart Disease Risk Factor (CHDRF) syndrome. The method includes administering, by a pharmaceutically effective mode, a drug composition having an opioidergic agent including an opiate antagonist, opiate having $\mu$-agonist activity or combination thereof, and an insulin secretagogue.

63 Claims, 1 Drawing Sheet

OTHER PUBLICATIONS

Garris, Nalmefene, An Opiate Antagonist, Effectively Modulates Insulin Receptor Binding in the Peripheral Tissues of C57BL/KSJ Mice, Medical Science Research, Elsevier Applied Science, Barking, GB, vol. 16, No. 6, 1988, pp. 301–302.

Drolet, et al., Endogenous Opioids Tonically Inhibit the Depressor Neurones in the Caudal Ventrolateral Medulla of Rabbits: Mediation through Delta and Kappa–Receptors, Neuropharmacology, Pergamon Press, Oxford, GB, vol. 30, No. 4, Apr. 1991 pp. 383–390.

McLauglin, et al., Influence of Nalmefene on Energy Balance and Glucose Regulation in Zucker Rats, Physiology and Behavior, Elsevier Science Ltd., Oxford, GB, vol. 37, No. 6, 1986, pp. 899–908.

McLaughlin, et al., Nalmefene Decreases Meal Size, Food and Water Intake and Weight Gain in Zucker Rats, Pharmacology Biochemistry and Behavior, Elsevier, US, vol. 19, No. 2, Aug. 1993, pp. 235–240.

McIntosh, et al., Effects of Selective Opioid Receptor Agonists and Antagonists During Myocardial Ischaemia, European Journal of Pharmacology, Amsterdam, NL, vol. 210, No. 1 Jan. 7, 1992, pp. 37–44.

Wexler, Naloxone Ameliorates the Pathophysiologic Changes which Lead to and Attend an Acute Stroke in Stroke–Prone/SHR, Stroke, American Heart Association, Dallas, TX, vol. 15, No. 4, Jan. 1984, pp. 630–634.

Giugliano, et al., Sensitivity to Beta–Endorphin as a Cause of Human Obesity, Metabolism, Clinical and Experimental, W.B. Saunders Co., Philadelphia, PA, vol. 36, No. 10, Oct. 1987, pp. 974–978.

Caldwell, et al., Actions of the Opioid Antagonist, Nalmefene, and Congeners on Reperfusion Cardiac Arrhythmias and Regional Left Coronary Blood Flow, Pharmacology, vol. 41, No. 3, 1990, pp. 161–166.

Bernardi, et al., Endogenous Opioid System in Acute Myocardial Infarction, Journal of Molecular and Cellular Cardiology, vol. 16, No. Suppl 2, 1984, p. 53.

Imai, et al., Effects of Opioid Antagonism in Congestive Heart Failure, Circulation (72, no. 4, Pt. 2, 1985) p. 248.

Levine, et al., Effect of Chronic Administration of Morphine and Nalmefene on Food Intake and Body Weight in Diabetic and Control Rats, Society for Neuroscience Abstracts, vol. 11, No. 1, 1985, p. 55.

Simpkins, et al., Efects of the Narcotic Antagonist Nalmefene on Spontaneous and Insulin–Induced Food Intake and Body Weight Gain in Male Rats, Society for Neuroscience Abstracts, vol. 11, No. 1, 1985, p. 59.

McLaughlin, et al., Glucose Insulin Food Intake and Body Weight Responses of Zucker Rats to Nalmefene and Opiate Antagonist, Diabetes Research and Clinical Practice, No. SUPPL 1, 1985, p. S372.

Szilagyi, "Psychosocial Stress Elevates Blood Pressure Via an Opioid Dependent Mechanism in Normotensive Rats, Clinical and Experimental Hypertension," Part A, Theory and Practice, U.S. 1991, vol. 13, No. 8, 1991, pp. 1383–1394.

Kurtz B. R. et al., "Nalmefene an Orally Active Opiate Antagonist Reduces Insulin Resistance and Caloric Intake in Obese Women with Polycystic Ovaries and Acanthosis Nigricans", Clinical Research, vol. 33, No. 2 Part 1, 1985, p. 615A.

Arias A. et al., "Influence of Selective Agonist K Peripheral ICI–204448 (ICI) on Blood Pressure of Rats Pretreated with Clonidine (CLO)" Methods and Findings in Experimental and Clinical Pharmacology, Prous, Barcelona, ES, vol. 19, No. Suppl. A, Nov. 1997, p. 92.

McCubbin J. A. et al., "Opiodergic Inhibition of Circulatory and Endocrine Stress Responses in Cynomolgus Monkeys: A Preliminary Study" Psychosomatic Medicine, Elsevier, New York NY, US, vol. 55, no. 1, Jan. 1993, pp. 23–28.

Spanagel R. et al., "Evidence That Nor–Binaltorphimine Can Function as an Antagonist at Multiple Opioid Receptor Subtypes" European Journal of Pharmacology, Amsterdam, NL, vol. 264, No. 2, Oct. 24, 1994 (Oct. 24, 1994), pp. 157–162.

Database Medline Online! US National Library of Medicine (NLM), Bethesda, MD, US; Nov. 26, 1990 (Nov. 26, 1990) Levine, A. S. et al. "Nor–binaltorphimine decreases deprivation and opioid–induced feeding." Database accession No. NLM1963567 & Brain Research, Netherlands Nov. 26, 1990, vol. 534, No. 1–2, pp. 60–64.

Database Embase (Online), Elsevier Science Publishers, Amsterdam, NL; 1987, Giugliano, D. et al. "(beta)–Endorphin and Islet Hormone Release in Type–2 Diabetes Mellitus. The effects of normoglycemia, enkephalin, naloxone and somatostatin", Database accession No. EMB–1988087121, XP002257952 abstract, & Diabete et Metabolisme, 1987 France, vol. 13, No. 6, 1987, pp. 618–624, ISSN: 0338–1684.

Khawaja, X. Z., et al., "Increased Sensitivity to Insulin–Releasing and Glucoregulatory Effects of Dynorphin A1–13 and U 50488h in ob/ob versus lean mice", Diabetes 1990 United States, vol. 39, No. 10, 1990, pp. 1289–1297, XP008023244, ISSN: 0012–1797.

Gupta, B., et al., "Glucose Homestatis and Drugs Acting on CNS: interactions with Antidiabetic Agents", Indian Journal of Pharmacology, vol. 26, No. 3, 1994, pp. 169–178, XP008022532, ISSN: 0253–7613, abstract p. 175, column 2, paragraph 3, tables 1–3.

Database Medline, (Online), US National Library of Medicine (NLM), Bethesda, MD, U.S., Sep. 19, 1986, Verspohle, E. J. et al. "The Significance of mu– and delta–Receptors in Rat Pancreatic Islets for the Opiod–Mediated Insulin Release", Database accession No. NLM2874836, XP002257627, abstract, & Biochimica it Biophysica Acta., Netherlands, Sep. 19, 1986, pp. 217–224, ISSN: 0006–3002.

Database Embase, (Online), Elsevier Science Publishers, Amsterdam, NL, 1982, Giugliano, D., et al., "Impaired Insulin Secretion in Human Diabetes Mellitus, The Effect of Naloxone–Induced Opiate Receptor Blocade", Database accession No. EMB–1982097228, XP002257628, abstract, & Diabetes 1982, U.S., vol. 31, No. 4, 1982, pp. 367–370.

Sachse, G., et al., "Opiates Influence Endocrine Pancreas Secretion", Diabetologia, Berlin, DE, vol. 21, No. 3, 1981, p. 444, XP008022526, ISSN: 0012–186X, abstract.

Ahren, B. "Effects of [beta]–Endorphin, Met–Ankephalin, and Dynorphin A on Basal and Stimullated Insulin Secretion in the Mouse", International Journal of Pancreatology, 1989, U.S., vol. 5, No. 2, 1989, pp. 165–178, XP008023242, ISSN: 0169–4197, abstract.

Leslie, R. D. G., et al., "Sensitivity to Enkephalin as a Cause of Non–Insulin Dependent Diabetes", Lancet, Little, Brown and Co., Boston, U.S., No. 8112, Jan. 17, 1979, pp. 341–343, XP008022453, ISSN: 0099–5355, whole document.

Database CA [Online], Chemical Abstracts Service, Columbus, Ohio, U.S., Ahlgren, Gunnar, "Insulin–Like Action of Morphine and Certain Morphine Derivatives", retrieved from STN Database accession No. 24:20275, XP002257953, abstract, & Skandianavisches Archiv Fuer Physiologie, 1930, 58, pp. 153–72.

Berkow, R., Fletcher A.J. (Eds.), Merck Manual of Diagnosis and Therapy, (175h Ed.), 1999 Merck Research Laboratories, New Jersey XP002257951, 236240, p. 175, tables 13–4.

Got, I, et al., "Medical Treatment in Diabetic Patients with Peripheral Occlusive Arterial Disease", Journal Des Maladies Vasculaires, 1993, France, vol. 18, No. 1, 1993, pp. 30–36, XP008023367, ISSN: 0398–0499, abstract, pp. 30–36.

Schultz, J. E. J. et al., "Morphine Mimics the Cardioprotective effect of Ischemic Preconditioning Via a Glibenclamide–Sensitive Mechanism in the Rat Heart", Circulation Research, 1996, U.S., vol. 78, No. 6, 1996, pp. 1100–1104, XP008022439, ISSN: 0009–7330, abstract.

Chance, W. T., et al., "Analysis of the Interaction of Naltrexone with Eating Following Adrenergic and Cholinergic Stimulation of the Hypothalamus", Neuropharmacology, vol. 21, No. 9, 1982, pp. 929–932, XP008022429, ISSN: 0028–3908, abstract.

Database Embase (Online), Elsevier Publishers, Amsterdam, NL, 1998, Swidan, S. Z., et al., "Effect of Blood Glucose Concentrations on the Development of Chronic Complications of Diabetes Mellitus", Database accession No. EMB–1998322939, XP002257629, abstract, & Pharmacotherapy, 1998, U.S., vol. 18, No. 5, 1998, pp. 961–972, ISSN: 0277–0008.

Green, I. C., et al., "Opiate–Prostagland in Interactions in the Regulation of Insulin Secretion from Rat Islets of Langerhans In–Vitro", Life Sciences, vol. 42, No. 21, 1988, pp. 2123–2130, XP008022434, ISSN: 0024–3205, abstract.

Awoke, S., et al., "Alterations of Plasma Opioid Activity in Human Diabetics", Life Sciences, Pergamon Press, Oxford, GB, vol. 34, No. 21, 1984, pp. 1999–2006 XP008022432, ISSN: 0024–3205, abstract.

McCormack, K. J., et al., "Opioid Receptors and Myocardial Protection do Opioid Agonists Possess Cardioprotective Effects?", Clinical Drug Investigation, ADIS International Auckland, NZ, vol. 15, No. 5, May 5, 1998, pp. 445–454, XP008022520, ISSN: 1173–2563, abstract.

Database Embase (Online), Elsevier Science Publishers, Amsterdam, NL, 1984, Yim, G. K. W. et al., "Opioids, Feedings, and Anorexias", Database accession No. EMB–1985026539, XP002257630, abstract, & Federation Proceedings 1984 U.S., vol. 43, No. 14, 1984, pp. 2893–2897.

Liang, Bruce T., et al., "Direct Preconditioning of Cardiac Myocytes Via Opioid Receptors and KATP Channels", Circulation Research, vol. 84, No. 12, Jun. 25, 1999, pp. 1396–1400, XP001165654, ISSN: 0009–7330, abstract.

Ferlito, S., Influenza Dei Peptidi Oppioidi Sul Metabolismo Glucidico, Progresso Medico, Leonardo Edizioni Scientifiche, Rome, IT, vol. 41, No. 11, 1985, pp. 639–655, XP008022534, ISSN: 0370–1514, abstract.

Caldara, R., et al, "Effect of Loperamide, A Peripheral Opiate Agonist, on Circulating Glucose, Free Fatty Acids, Insulin C–Peptide and Pituitary Hormones in Healthy Man", European Journal of Clinical Pharmacology, Springer Verlag, DE, vol. 21, No. 3, 1981, pp. 185–188, XP008022524, ISSN: 0031–6970.

Arioglu, E., et al. "Efficacy and Safety of Trogliatazone in the Treatment of Lipodystrophy Syndromes", Annals of Internal Medicine, New York, NY, vol. 133, No. 4, Aug. 15, 2000, pp. 263–274, XP000985954, ISSN: 0003–4819.

Martinez, E., et al., "Metabloic Abnormalities and Body Fat Redistribution in HIV–1 Infected Patients: The Lipodystrophy Syndrome", Current Opinion on Infectious Diseases, Current Sciences, GB, vol. 12, No. 1, Feb., 1999, pp. 13–19, XP001098488, ISSN: 0951–7375.

Liu, et al., "Activation Of Opioid $\mu$–receptor By Loperamide To Lower Plasma Glucose In Streptozotocin–induced Diabetic Rats", Neuroscience Letters, vol. 265, No. 3, pp. 183–186, (Apr. 23, 1999).

Riepl, et al., "Pancreatic Polypeptide Release Induced By Ceruletide, Sham Feeding, And Hypoglycemia Is Suppressed By Loperamide", European Journal of Clinical Investigation, vol. 23, No. Suppl. 1, p. A10, (1993).

Marsboom, et al., "Loperamide (R 18 553), A Novel Type Of Antidiarrheal Agent", Janssen Pharmaceutica, Research Laboratoria, vol. 24, No. 10, pp. 1645–1649, (Oct. 1974).

Carr, et al., "The Role Of Opioids In Feeding And Reward Elicited By Lateral Hypothalamic Electrical Stimulation", Life Sciences, Pergamon Press, vol. 33, No. Suppl. 1, pp. 563–566, (1983).

Gautret, et al., "Vagally Mediated Reflex And Cardiac Slowing Induced By Loperamide In Rats", European Journal of Pharmacology, vol. 107, No. 2, pp. 157–160, (1985).

Riepl, et al., "Suppression Of Vagus–Mediated Pancreatic Polypeptide Release By The $\mu$–Opiate Receptor Agonist Loperamide in Man", British Journal of Clinical Pharmacology, vol. 42, No. 3, pp. 371–377, (1996).

Green, et al., "Effect of Enkephalins And Morphine On Insulin Secretion From Isolated Rat Islets", Diabetologia, vol. 19, No. 2, pp. 158–161, (Aug. 1980).

Ahlgren, Gunnar, "Insulin—Like Action Of Morphine And Certain Morphine Derivatives", Skank, Arch Physiol, 58, pp. 153–72, (1930).

Green, et al., "Opioid Peptide Effects on Isolated Hepatocytes And Islets Of Langerhans", International Congress Series, 700 (Diabetes 1985), pp. 258–62, (1986).

Bailey, et al., "Increased Responsiveness To Glcoregulatory Effect of Opiates On Obese–Diabetic ob/ob/Mice", Diabetologia, vol. 30, No. 1, pp. 33–37, (Jan. 1987).

The Merck Index 10th Ed., 1983 pp. 491–492.

The Merck Index 14th Ed., 1996 p. 1052 [Metyrosine].

R. Landgraf et al.; "Prolactin: A Diabetogenic Hormone", Diabetologia 13, 1977, pp. 99–104, 1976.

The Pharmacological Basis of Therapeutics, Seventh Edition (Chapter 18, p. 383), 1985.

Atkinson et al., "Effects of Long–Term Therapy with Nultrexone on Body Weight in Obesity" Clin. Pharmacol. Ther. (10/85) pp. 419–422.

J.R. Givens et al.; "Reduction of Hyperinsulinemia" J. Clin. Endocr. & Metab. 64/2, (1987) pp. 377–382.

G. R. Van Loon et al.; Endocrinology; vol. 109, p. 46, 1981.

R. Vink et al.; "K–Opioid Antagonist Improves Cellular Bioenergetics and Recovery After Traumatic Brain Injury" Am. J. Physiol. 261, 1991.

Sohel et al. "Influence of Adrenergic Blockers and Antilipemic Agents on Pharmacodynamic Actions of Morphine in Carbon Tetrachloride–Treated Rats." Toxicol Appl Pharmacol 27(3) :477–483, Mar., 1974.

Stern et al. "Lack of Awareness and Treatment of Hyperlipidemia in Type II Diabetes in a Community Survey." JAMA 262 (3) :360–4, Jul., 1989.

Herz A. "Bidirectional Effects of Opioids in Motivational Processes and the Involvement of D1 Dopamine Receptors." NIDA Res Monogr 1988;90:17–26.

Herz A.; "Opioid Reward Mechanisms: A Key Role in Drug Abuse?" Can J Physiol Pharmacol 76, 3:252–8, 1998.

Pan Z.Z.; "mu–Opposing Actions of the Kappa–Opioid Receptor" Thrends Pharmacol Sci.; 19, 3: 94–8, 1998.

Porotoghese, et al.; "Binaltorphimine and Nor–Binal Torphimine, Potent and Selective k–Opioid Receptor Antagonists" Life Sciences 40: 1287–92, 1987.

Jones et al.; Journal of Medicinal Chemistry 41, 25: 4911–4, 1998.

Merz et al.; Advances in biochemical psychopharmacology, vol. 8:91–107, 1974.

Porotoghese et al.; "TENA, A Selective Kappa Opioid Receptor Antagonist" *Life Sciences* 36:801–5, 1984.

Lewis J. W.; "Buprenorphine" Drug and Alcohol Dependence; 14:363–372, 1985.

McQuay J.J. et al.; "Clinical Effects of Buprenorphine During and After Operation" Br J. Anaesth; 52:1013–19, 1980.

Ruppin H.; "Loperamide—A Potent Antidiarrhoeal Drug with Actions Along the Alimentary Tract" Aliment Pharmacol Ther 1987, 1(3): 179–190.

Caldara R. et al.; "Effect of Loperamide, a Peripheral Opiate Agonist, on Circulating Glucose, Free Fatty Acids, Insulin, C–Peptide and Pituitary Hormones in Healthy Man" Eur. J. Clin Pharmacol; 21, 3:185–8, 1981.

Buzi F. et al.; "Loperamide Test: a Simple and Highly Specific Screening Test for Hypercortisolism in Children and Adolescents" Acta Paediatr; 86, 11: 1177–80, 1997.

Foss et al.; "Restoration of Glucose Homeostasis in Insulin–Dependent Diabetic Subjects"; Diabetes, 31:46–52, 1982.

Pfeifer et al.; "Insulin Secretion in Diabetes Mellitus"; The American Journal of Medicine, 70:579–588, 1981.

Felber et al.; Effect of a 3–Day Fast on Glucose Storage and Oxidation in Obese Hyperinsulinemic Diabetics; Metabolism, 30, 2; 184–189 and Diabetologia, 20:39–44, 1981.

Edelman, S.V.; "Prescribing Oral Antidiabetic Agents: General Condsiderations"; Clinical Diabetes 16,1:37–40, 1998.

* cited by examiner

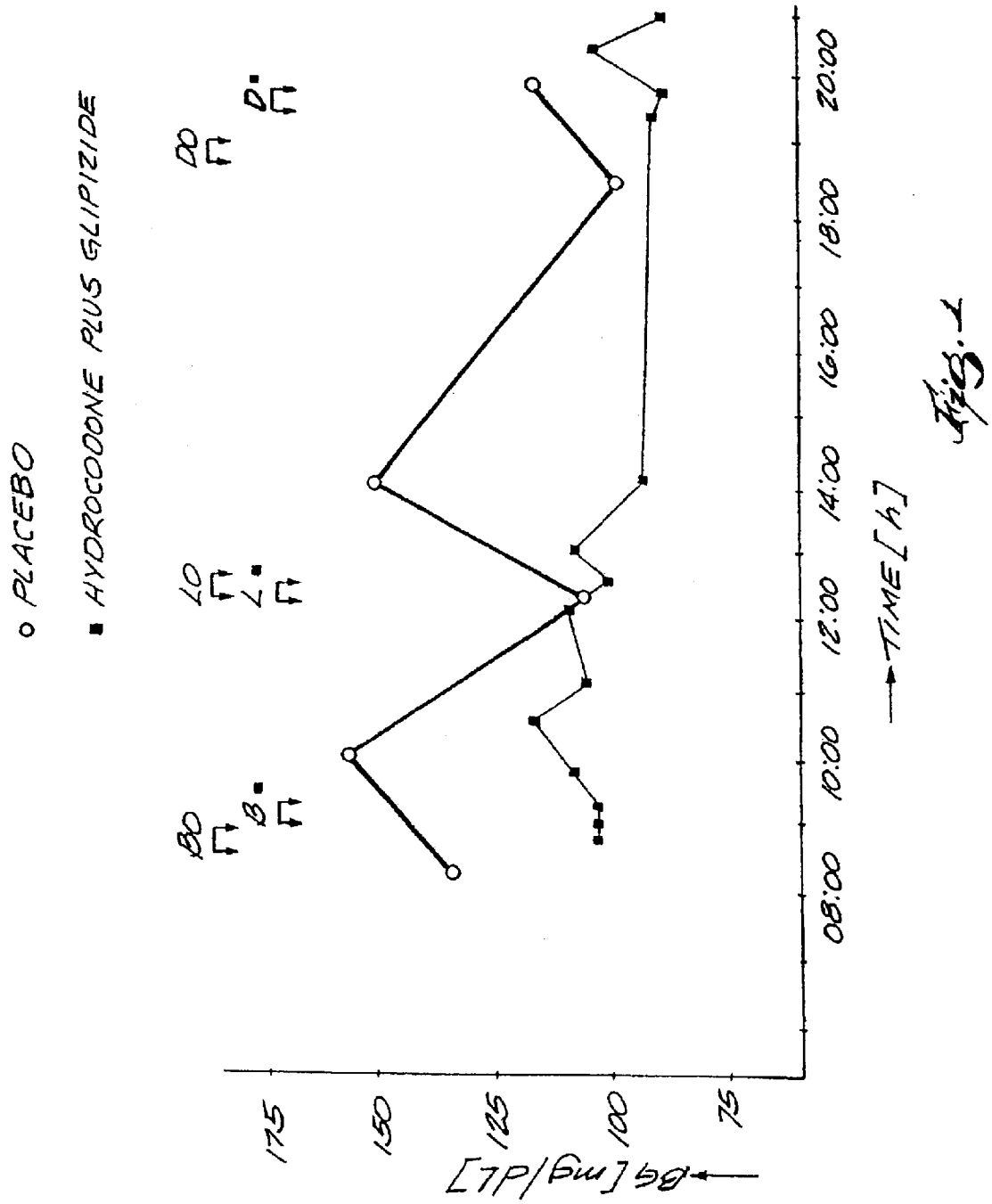

METHOD OF TREATING THE SYNDROME OF CORONARY HEART DISEASE RISK FACTORS IN HUMANS

CROSS-REFERENCE TO RELATED APPLICATION

This application is a continuation-in-part of U.S. application Ser. No. 09/878,834 filed on Jun. 11, 2001, which issued as U.S. Pat. No. 6,528,520 on Mar. 4, 2003, and is a continuation-in-part of and claims priority to U.S. application Ser. No. 09/639,061 filed on Aug. 15, 2000, which issued as U.S. Pat. No. 6,262,062 on Jul. 17, 2001.

BACKGROUND OF THE INVENTION

Coronary Heart Disease Risk Factors (CHDRFs) are major causes of death in the industrialized world. CHD risk factors include Type 2 Diabetes (and its precursor, Impaired Glucose Tolerance (IGT)), hyperlipidemia or dyslipidemia, overweight, obesity and essential hypertension, i.e., a form of hypertension that occurs without a discoverable organic cause. The CHDRF syndrome may, therefore, be defined as a group of interrelated disorders: Type 2 Diabetes, IGT, Dyslipidemia, Overweight, Obesity and essential hypertension. It has also become apparent that Type 2 Diabetes, by itself, represents a syndrome of various, in part sequential, disease states which interact with other components of the CHDRF syndrome. However, the exact interrelationships between the disease states that make up these syndromes is not fully understood. A wide variety of chemical and physical abnormalities associated with these syndromes exist. They include elevations in fasting blood glucose and gluconeogenesis in spite of significant increases in fasting insulin and C-peptide concentrations and increases in lipogenesis. Typically associated with lipogenesis are increases in levels of fasting Free Fatty Acid (FFA), fasting triglycerides (TG) and total cholesterol concentrations, increases in levels of fasting Low Density Lipoprotein (LDL)-cholesterol, decreases in levels of fasting High Density Lipoprotein (HDL)-cholesterol, an increased LDL/HDL ratio, increases in body weight and increases in systolic and diastolic blood pressure.

Although these syndromes are interrelated and typically result from derangements in nutrient metabolism, all the associated symptoms may not be present in individual patients. Accordingly, in some patients lipid metabolism problems may predominate, while in others, carbohydrate metabolism problems may be predominant. While these factors, which lend one aspect of the syndrome to dominate over another, are not well understood, it is clear that each portion of the syndrome, or combinations of portions of the syndrome, represents risk factors in coronary heart disease.

Insulin Resistance/Beta-Cell Dysfunction/Type 2 Diabetes/CHDRF Syndrome

Common denominators in the etiology of the syndromes of Type 2 Diabetes and the CHDRFs appear to be Insulin Resistance (IR) and Beta-Cell Dysfunction. IR is characterized as a state in which a normal amount of insulin produces a subnormal biological response in carbohydrate metabolism. This may be the case for subjects afflicted with the non-insulin-dependent diabetes form of Type 2 Diabetes, in pre-diabetic subjects affected by Impaired Fasting Glucose (IFG) or Impaired Glucose Tolerance (IGT), and in overweight and obese subjects. These subjects require (and endogenously produce) higher than normal levels of insulin to compensate for their insulin resistance and Beta-Cell Dysfunction to normalize their blood glucose levels. Traditionally, IR has been expressed as the insulin/glucose ratio (I/G). More recently, several more complex models have been proposed to define Insulin Resistance or the Insulin Sensitivity Index. Only recently have other biological functions of insulin become the focus of more intense scientific interest, e.g. the role of insulin in endogenous lipogenesis. Although an interaction between insulin resistance and the CHDRF components has been established, the cause and effect relationship between insulin resistance, obesity, dyslipidemia and IGT/Type 2 Diabetes is still subject to debate. IR increases FFA and Triglyceride (TG) levels, which further contribute to IR, thereby creating a vicious circle. Therapeutic modalities for lowering any one of the lipid fractions in dyslipidemia have not proven capable of correcting the entire hyperlipidemic complex with a single therapeutic agent.

Compared to Type 1 (juvenile) Diabetes, the Type 2 Diabetes syndrome, particularly its non-insulin-dependent mellitus (NIDDM) forms, is characterized by relatively inadequate endogenous insulin concentrations. However, insulin concentrations in Type 2 diabetics may, in fact, be higher than in the normal population. A possible explanation for this apparent discrepancy is that Type 2 diabetics, as well as subjects afflicted with IFG, IGT, Overweight or Obesity typically require more insulin to control their blood sugar levels. Temporary increases in certain diabetogenic mediators, such as glucagon, growth hormones and catecholamines may initially cause the requirement for more insulin. These mediators communicate their specific control functions as agonists to target tissue or cells through compatible cell bound receptors. Continued, long term agonist load eventually leads to 'down-regulation' of such receptors, i.e. the receptor response and/or sensitivity are decreased. Depending on the agonist involved, this mechanism can lead to tolerance or addiction. As a result, increasing doses are required to achieve the same effect. Antagonists have equivalent receptor specificity as their agonist counterparts, but do not convey any agonist-type control message. In contrast to agonists, prolonged exposure of such receptors to their specific antagonists can restore receptor response or sensitivity, a process called receptor 'up-regulation'.

As long as any agonists load by mediators, such as hormones, neuro-transmitters or neuro-modulators prevails for infrequent, short durations, the respective receptors for such mediators can 'up-regulate' between such temporary agonist loads. In other words, the receptors can resume their normal sensitivity between 'receptor-ligand' interactions. The early stage of IR may be characterized by temporary increases in diabetogenic mediators such as catecholamines, endogenous opiates, cortisol and/or glucagon.

Another early pathophysiologic indicator of the emergence of the CHDRF Syndrome is a condition called Beta-Cell Dysfunction. Non-diabetics experience a bi-phasic insulin response to an oral glucose challenge, i.e. an acute, first phase governed by a rise in blood glucose, and second, proportional phase characterized by a more sustained insulin release, following, in a quasi proportional manner, the post-prandial glucose excursion. Overweight and IGT subjects already have a significantly reduced first phase insulin release, which virtually disappears altogether once the subject becomes obese and or diabetic. This condition exaggerates the Insulin Resistance related hyperglycemia and hyperinsulinemia and accelerates the severity of the CHDRF Syndrome.

A pharmacologic restoration of the vitally important first phase insulin release has, to this date, been an elusive scientific undertaking.

Resistance to the action of insulin in the control of glucose may not carry over to the action of insulin on lipogenesis. Even though the individual is resistant to the action of insulin in controlling glucose, the response of lipid metabolism to insulin may remain at the normal level. As temporary agonist 'loads' become more frequent or sustained, the affected receptors will down-regulate. As a result, IR may become a permanent metabolic burden and, with additional diabetogenic factors, such as cortisol, may accelerate progressive increases in hepatic gluconeogenesis (GNG) and glucose production (GP). The IR dependent insulin excess in the face of hyper-gluconeogenesis caused hyperglycemia then becomes a blueprint for hyper- or dyslipidemia, overweight and obesity. Gradually, the β-cells' secretory capacity to produce and secrete insulin will diminish, resulting in a slow but steady rise in fasting glucose levels until, eventually, such secretory capacity will be exhausted, at which time the subject becomes 'insulin dependent', i.e. dependent on exogenous insulin injections.

Dyslipidemia

Dyslipidemia is characterized by any of the following, and combinations thereof: elevated levels of total and LDL-cholesterol, elevated levels of TG, a high LDL/HDL ratio and elevated levels of FFA and low levels of HDL-cholesterol. Lipid metabolism is rather complex. While it is clear that dyslipidemia is associated with the development of coronary heart disease, there is no clear understanding of the pathogenic causes and pathways leading up to the manifestation of the various lipid disorders. The relative roles of lipid ingestion versus endogenous lipogenesis in the etiology of lipid abnormalities have not been fully understood.

Overweight/Obesity

Obesity is a disease of major proportions and severe economic consequences. No longer is obesity considered merely a physical or cosmetic inconvenience. Obesity is second only to cigarette smoking as a preventable cause of premature death, and its complications add in excess of $100 billion to U.S. health care costs. Obesity can not be treated effectively by willpower alone, and currently available pharmaceutical drugs are only marginally effective. Moreover, several obesity drugs have recently been withdrawn from the market because of their risk of potentially fatal side-effects, e.g. pulmonary hypertension or heart defects in connection with dexfenfluramine, fenfluramine or phentermine.

Six out of ten people (approximately 130 million) in the United States are overweight, close to 90 million are clinically obese and 22 million are morbidly obese.

The definitions of obesity and overweight are somewhat arbitrary. The symptoms of overweight and obesity are characterized by excessive body fat, i.e. the body contains a level of fat beyond what is considered normal. Body weight in relationship to height and build is used as a surrogate measure of obesity and overweight. Being 20% over the standard height weight tables is considered obese. The body mass index (BMI) is commonly used in defining normal weight. The BMI is calculated by dividing a subject weight in kilograms by the square of height in meters ($kg/m^2$) or ($lbs. \times 705/inches^2$). A BMI of 25 is considered normal, a BMI of 26–29 is considered overweight, a BMI of 30–40 is obese, and a BMI>40 is considered morbid. A therapeutic intervention is considered effective if it produces a weight reduction of >10%, or a reduction by >5% if 'co-morbid' factors are also improved, e.g. any of the blood analyte concentrations related to IGT, Type 2 Diabetes or dyslipidemia.

Despite the recognized interaction between the various CHD risk factors, the pharmaceutical modalities currently available to treat the symptoms of Type 2 Diabetes generally have had no beneficial effect on hyper- or dyslipidemia; in fact, some of the medicines widely used to treat Type 2 Diabetes, e.g. sulfonylureas, tend to increase hyperlipidemia and may, therefore, further contribute to overweight and obesity, thereby increasing the CHD risk. Conversely, medicines presently available to treat various forms of hyper- or dyslipidemia have little or no impact on IFG, IGT, Type 2 Diabetes, overweight or obesity.

Moreover, no single pharmaceutical agent has been able to treat and correct the entire complex of hyper- or dyslipidemia. Drugs such as clofibrate/gemfibrozil can lower TG levels, but have little or no effect on FFA levels, and no effect on total cholesterol levels. Other drugs may shift the proportion of cholesterol found in the form of low and high density lipoprotein cholesterol. For example, certain drugs may actually increase already elevated levels of low density lipoprotein cholesterol. On the other hand, drugs like lovastatin lower the levels of both total and low density lipoprotein cholesterol, while only slightly increasing the level of high density lipoprotein cholesterol. However, these drugs have no effect on FFA and little or no effect on TG levels.

As a result, it is desirable to provide an improved method for treating the syndrome of coronary heart disease risk factors. A new method for treating the early morning rise in hepatic gluconeogenesis and endogenous glucose production is also desired. In other words, an improved method of treatment is desired that lowers high glucose levels resulting from rises in gluconeogenesis and glucose production, and impaired insulin secretion in patients afflicted with CHD risk factors in humans. A new method is also desired wherein the administration of a drug composition does not require a priming dose.

SUMMARY OF THE INVENTION

The present invention provides improved methods of treating a human suffering from one or more conditions included within the Coronary Heart Disease Risk Factor (CHDRF) syndrome. The invention provides a method including administering, by a pharmaceutically effective mode, a drug composition comprising an opioidergic agent (e.g. on opiate antagonist, an opiate having $\mu$-agonist activity, or a combination thereof, and an insulin secretagogue.

The invention further provides a method of treating a human suffering from one or more conditions included within the Coronary Heart Disease Risk Factor (CHDRF) syndrome by administering, by a pharmaceutically effective mode, a drug composition comprising an opiate antagonist and an insulin secretagogue.

The invention further provides a method of treating a human suffering from one or more conditions included within the Coronary Heart Disease Risk Factor (CHDRF) syndrome by administering, by a pharmaceutically effective mode, a drug composition comprising an opiate agonist and an insulin secretagogue.

Before embodiments of the invention are explained in detail, it is to be understood that the invention is not limited in its application to the details of the compositions and concentrations of components set forth in the following description. The invention is capable of other embodiments and of being practiced or being carried out in various ways. Also, it is understood that the phraseology and terminology used herein is for the purpose of description and should not be regarded as limiting.

The patents, references and articles cited herein are hereby fully incorporated by reference.

BRIEF DESCRIPTION OF DRAWING

FIG. 1 is a graph showing the daily blood glucose profile of a 72-year subject afflicted with Type 2 Diabetes and dyslipidemia after treatments with an opioidergic drug composition in combination with an insulin secretagogue. The blood glucose (BG) of the subject was measured in mg/dL over several time intervals measured in hours (h).

DETAILED DESCRIPTION OF THE INVENTION

As used herein, the term "insulin secretagogue" is meant to refer to any drug composition which stimulates, participates in the stimulation of, or potentiates, the secretion of insulin by the pancreatic Beta-Cells. Insulin secretagogues include insulinotropic agents and insulin secretion or release potentiators. Examples are provided below.

As used herein, the terms "opioids," "opioid agonists," "opiate agonists," "opiates having agonist activity" and "agonists" are meant to refer to opioid-like substances, natural or synthetic, that bind to centrally and/or peripherally located opioid receptors to produce an agonist action.

As used herein, the terms "$\mu$", "$\delta$" and "$\kappa$" refer to the specific types of opiate receptors of cells such as brain, spinal cord and large intestine.

As used herein, the terms "opiates having $\mu$-agonist activity," "opioids having $\mu$-agonist activity" and "$\mu$-agonists" are meant to refer to opioid-like substances, natural or synthetic, that bind to the $\mu$ opiate receptor to produce an agonist action.

As used herein, the terms "opioid antagonists," "opiate antagonists," "anti-opioids," "antiopiates," "opiates having antagonist activity" and "antagonists" are meant to refer to opioid-like substances that bind to opioid receptors, but produce little or no agonist activity.

As used herein, the terms "opiates having $\kappa$ antagonist activity," "opioids having $\kappa$ antagonist activity" and "$\kappa$ antagonists" are meant to refer to opioid-like substances that bind to the $\kappa$ opiate receptor, but produce little or no agonist activity.

As used herein, the terms "opioidergic agent" and "opioidergic drug composition" are meant to refer to any of the above opioid-like substances as well as combinations thereof.

"Pharmaceutically effective modes" are meant to include, but not be limited to, the application of a drug composition as a solution in an innocuous pharmaceutically acceptable solvent, as an emulsion, as a suspension, as a dispersion in suitable carriers, as a patch or in the form of pills, or capsules with solid, liquid or gel carriers, and other such methods well-known in the art. The formulations of this invention may include pharmaceutically acceptable excipients such as stabilizers, anti-oxidants, binders, coloring agents, emulsifiers, and other such excipients well-known in the art. The drugs and drug compositions comprising the agonists and antagonists described above and below, may be administered in any pharmaceutically effective mode.

Opiate antagonists are molecular structures similar to opiates but do not have appreciable direct agonist activity. Antagonists have the ability to reduce or prevent the receptor binding of opiate agonists, thus neutralizing their biologic effect. Anti-opioids, or narcotic antagonists, are characterized by their ability to displace narcotic agonists from the respective receptors. Since most narcotics possess several agonist actions, e.g. $\mu$, $\delta$, and $\kappa$, anti-opioids may possess antagonist capabilities for those (and other) receptors as well. In general, the antagonist activity, or effectiveness of anti-opioids is not equal at the various receptor sites and may vary significantly, often times by more than an order of magnitude. For example, the $\mu$ receptor binding effectiveness for naltrexone may be 12 times higher than its effectiveness to bind to a $\kappa$ receptor, which may result in a 12-fold increase of agonist displacement at the $\mu$ receptor over the $\kappa$ receptor. Since the $\mu$ receptor is known to control (amongst others) euphoria, a suppression of this action 12-fold over any action controlled by $\kappa$, e.g. for various metabolic functions can actually result in disphoria, if the antiopioid dosage has to be increased to achieve the desired effect at the $\kappa$ site.

$IC_{50}$ is defined as the concentration of a compound at which 50% of the standard molecule is displaced from the target receptor. For each receptor there is a prototype ligand. To measure the $IC_{50}$ for a given anti-opioid, one measures the concentration of the anti-opioid which will drive 50% of the prototype ligand from the target receptor. For the $\mu$ receptor the prototype ligand is DHM (dihydromorphine). For the $\delta$ receptor, the prototype ligand is DADLE (D-Ala+D-Leu-Enkephalin), and for the $\kappa$ receptor, the prototype ligand is EKC (ethylketocyclazocine).

There are several types of opiate receptor sites and the opiate antagonists do not, generally, have an equipotent effect on all the different receptor sites. In evaluating opiate antagonists for use in the treatment of any or all of the CHDRE'S, their interaction with the $\mu$, $\delta$, and $\kappa$ opiate receptors is most important. Opiate antagonists, such as naloxone and naltrexone, which exert their greatest effect, by approximately an order of magnitude, upon the $\mu$ receptors, may be used to treat the CHDRFS, but may have undesirable CNS side effects due to their dominant $\mu$ receptor antagonism versus the $\delta$, and $\kappa$ opioid receptors, resulting in an enhanced $\kappa$ agonist action. Opioid antagonists which have approximately equal effects on the $\mu$, $\delta$, and $\kappa$ receptors, such as nalmefene, diprenorphine and CHMMO, are more useful for the treatment of CHDRFS in humans. It has, further, been discovered that inhibition of the $\kappa$ opiate receptor is important in determining the effect of an anti opioid on the CHDRFS. It is, therefore, preferred that the anti-opioids have an effect upon the $\kappa$ opiate receptor as strong as or stronger than effect upon the $\mu$, and $\delta$ opiate receptors. Since a strong inhibitory effect means that the anti-opioid is effective at low concentrations, it is desirable that the anti-opioids have a lower $IC_{50}$ for the $\kappa$ opiate receptor than for the $\mu$, and $\delta$ opiate receptors.

The relationship between the $IC_{50}$ levels for the $\mu$, $\delta$, $\kappa$ opiate receptors may also be expressed in terms of a ratio. For example, if the $IC_{50}$ level for the $\mu$, opiate receptor is within a factor of 3 of the $IC_{50}$ level for the $\delta$ opiate receptor then the ratio of the $IC_{50}$ level for the $\mu$, opiate receptor to the $IC_{50}$ level for the $\delta$ opiate receptor may be expressed in the following manner: $1/3 < (IC_{50} \delta/IC_{50}\mu) < 3$. The preferred anti-opioids or anti-opioid combinations for use in the treatment of CHDRFC have a ratio of $IC_{50}$ for the $\kappa$ opiate receptor to the $IC_{50}$ for the $\mu$ or $\delta$ receptors of 10 or less and most preferably 3 or less. These preferred compositions may be expressed as a ratio of $IC_{50}$ values: $\{(IC_{50} \kappa/IC_{50}\mu)<10\}$, and $\{(IC_{50} \kappa/IC_{50} \delta)<10\}$; and the most preferred compositions have $IC_{50}$ values: $\{(IC_{50} \kappa/IC_{50}\mu)<3\}$, and $\{(IC_{50} \kappa/IC_{50} \delta)<3\}$. A $\kappa$ antagonist such as nor-binaltorphimine is useful in the treatment of any or all of the conditions, which make up the CHDRFS. It may be used alone, or in combination with other anti-opioid drugs. When used as part of a combination drug, it serves to add further inhibition of the κ opioid receptors to the properties of the combination.

Metformin hydrochloride is a non-sulfonylurea type antihyperglycemic agent, which improves glucose tolerance in type 2 diabetic subjects, primarily by decreasing hepatic gluconeogenesis and glucose production (Edelman, S. V.: Clinical Diabetes; 16,1:37–40). The major side effects are potential lactic acidosis, and the impact of the required massive therapeutic doses on liver and kidney function. Metformin is, therefore, contraindicated for patients with hepatic and renal insufficiency, which is aggravated by the fact that a typical daily dose ranges between 1,500 and 2,500 mg.

During the investigations into, and development of, non-addictive morphine based analgesics, typically requiring a combination of agonistic and antagonistic actions at various opiate receptor sites, i.e. $\mu$, $\delta$ and κ receptors, a variety of so-called 'pure' antagonists have evolved as by-products, and some of these narcotic antagonists, or anti-opioids, have been shown to have potential in the treatment of a variety of disease conditions.

U.S. Pat. No. 4,272,540 discloses various 14-methoxy substituted 3-hydroxy or 3-methoxy-6-one morphinans, which are variously useful as analgesics, narcotic antagonists, and mixed analgesics and narcotic antagonists.

U.S. Pat. No. 4,451,470 discloses 14-fluoromorphinans which are useful as analgesic, narcotic antagonists and/or anorexigenic agents.

U.S. Pat. No. 4,478,840 discloses 17-cycloalkylmethyl-4,-5α-epoxymorphinan-3,14-diol compounds useful for suppression of appetite in mammals.

U.S. Pat. No. 4,619,936 discloses pharmaceutical compositions containing (5α,6α)7,8-didehydro-4,5-epoxy-17-(2-propanyl)-morphinano-3,6-diol for the purpose of appetite reduction.

U.S. Pat. No. 4,882,335 discloses a method useful as an adjunct in the treatment of alcoholism. The method involves having the patient drink alcoholic beverages, while an opiate antagonist blocks the positive reinforcement effects of ethanol in the brain.

U.S. Pat. No. 5,086,058 discloses a method for treating alcoholism. The method involves having the patient drink alcoholic beverages while nalmefene, an opiate antagonist, blocks the positive reinforcement effects of ethanol in the brain.

In order to address the dramatic increases in diabetes, obesity and other CHDRFs, and their effects on patient morbidity/mortality and national health care expenditures, the focus of pharmaceutical research is shifting from post symptomatic stabilization to prevention and intervention. The pathophysiology of the syndrome CHDRFs is a progressive process with changing conditions, as physiologic control functions become strained, exhausted and, eventually, supplemented or replaced by other compensatory mechanisms. Therefore, the different stages in this progression necessitate different interventive measures tailored to retain or restore those functions still viable.

U.S. Pat. No. 5,727,570 discloses a method of treatment of humans suffering from hyperlipidemia by administering a drug composition selected from a group consisting of opiate antagonists and drugs which substantially equally reduce the amount of catecholamines bound to catecholamine binding sites. In a model case study, conducted with a pure anti-opioid, this method was applied during the pre-diabetic stage of IFG combined with IR, and resulted in significant improvements in all carbohydrate and lipid control functions, restoring all relevant Blood Analyte Concentrations (BAC) to normal physiologic levels, with a reduction of FBG to 95 mg/dL.

U.S. Pat. No. 5,878,750 discloses a method of treating humans suffering from the Coronary Heart Disease Risk Factor syndrome by administering a drug composition selected from the group of opiate antagonists or anti-opioids and drugs which substantially equally reduce the amounts of catecholamine bound to all catecholamine binding sites. A model case study involved the administration of a pure opioid antagonist to an overweight subject with early stage Type 2 Diabetes and dyslipidemia, having a fasting blood glucose level (FBG) of 138 mg/dL, which is exceeding the criteria for IFB and IGT. Although all carbohydrate and lipid metabolism related BACs, as well as overweight and hypertension, showed significant improvements, all were restored back to normal, with the exception of FBG which, despite its 13% improvement, only dropped from 138 mg/dL to 120 mg/dL, still within the IGT range.

U.S. Pat. No. 6,026,817 discloses a method of treatment of humans suffering from the syndrome of Coronary Heart Disease Risk Factors which comprises the steps of 1) administering a priming dose of a drug composition selected from the group consisting of opioid antagonists and 2) administering a maintenance dose of said drug. It also discloses a method of combining said dosing sequence with a method of improving the balance between or equalizing the IC-50 values of an anti-opioid composition for its respective target receptors, by adding small amounts of one or more drugs with opioid agonist activity whereby the agonist competes with the antagonist for the particular receptor, and diminishes, but does not totally remove any of the respective antagonist properties of the anti-opioid composition.

The present invention provides an improved method of treating the Syndrome of CHD risk factors, by the administration of insulin secretagogues in combination with an opioidergic drug composition. The syndrome of CHD risk factors includes the various disease states of Type 2 Diabetes, as well as hyper- or dyslipidemia, overweight, obesity and/or essential hypertension. The disease states of the Type 2 Diabetes syndrome progress through insulin resistance (IR) and Beta-Cell dysfunction, impaired fasting glucose (IFG), excessive hepatic gluconeogenesis (GNG) and glucose production (GP), and impaired glucose tolerance (IGT) to the clinical form of Type 2 Diabetes. The improved method provides a treatment for any number of individual conditions within the syndromes of CHDRF and Type 2 Diabetes. This invention also provides a method of treating the early morning increase in gluconeogenesis and increased glucose production which, in the presence of relatively impaired insulin secretion, results in elevated fasting glucose levels. This invention further provides a method to restore the physiologic acute, first phase insulin release.

Non-glucose dependent insulin secretagogues, such as sulphonylureas, stimulate insulin secretion regardless of the blood glucose level and are, therefore, prone to produce potentially deleterious hypoglycemia, particularly so, because such insulin secretagogues primarily increase the second phase insulin release with no improvement in first phase insulin secretion.

This invention of administering, by a pharmaceutically effective mode, opioidergic drug compositions in combination with non-glucose dependent insulin secretagogues, such as sulphonylureas, can confer a more glucose dependent, bi-phasic insulin release pattern on such secretagogues, and significantly reduce the likelihood of producing hypoglycemia.

Another aspect of this invention is to provide an improved first pass insulinization of the liver, resulting in a restoration of enzyme functions involved in hepatic fuel processing, including carbohydrate oxidation and storage.

Drugs which are useful in the methods of the present invention, i.e. improved methods for treating humans suffering from CHD risk factors, include opioid drug compositions of non-selective or selective opioid antagonists, with or without the supplementation of centrally or peripherally acting $\mu$-agonist activity, and in combination with insulin secretagogues, including insulinotropic agents and/or insulin secretion or release potentiators. Insulin secretagogues include, but are not limited to, sulphonylureas, such as tolbutamide, chlorpropamide, glimepiride, glipizide, and glyburide, (all listed in Merck Index, $12^{th}$ Edition, 1996), repaglinide, (Raskin P et.al.: Diabetes Care 23[7]:979–83), meglitinides, morphilinoguanide and pramlintide (Evans A J and Kreutz A J: Drugs RD 2[2]:75–94), acetylcholine (Tae Niwa et. al.: Diabetes 47: 1699–1706), muscarinic agonists, e.g. carbachol (Hiriart M and Ramirez-Medeles M C: Mol Cell Endocrinol 93[1]: 63–9), bethanechol (Physicians Desk Reference [PDR]), beta-L-glucose pentaacetate, (Malaisse W J et.al.: American Journal of Physiology 276[6/1]: E993–E1006), chiro-inositol (Larner J. et. al. U.S. Pat. No. 5,428,066), myo-inositol (Szkudelski T and Kandulska K.: Arch. Physiol. Biochem. 107[4]:334–7), GIP (Kindmark H et.al.:J Clin Endocrinol Metab 86[5]:2015–9), GLP-1 and Extendin-4 (Parkes D G et. al.: Metabolism 50[5]:583–9).

It is preferred to administer the $\mu$-agonist composition concurrently with the opioid antagonist drug compositions and select combinations having compatible biologic half-lives in order to facilitate the matching of their respective pharmacodynamics.

Bi-directional effects of opioids are known to exist, in particular between $\mu$ and $\kappa$ agonists, such as $\mu$-agonists producing euphoria and $\kappa$ agonists producing the opposite, namely disphoria. Conversely, $\mu$ antagonists can antagonize euphoria and enhance the effect of the $\kappa$ agonist, while the $\kappa$ antagonist can produce or enhance euphoria. Examples of this phenomenon also include the opposing effects of $\mu$ and $\kappa$ opiates in motivational processes (Herz A.: NIDA Res Monogr 90:17–26), or in opioid reward mechanisms (Herz A.: Can J Physiol Pharmacol 76,3:252–8), and other $\mu$-opposing actions of the $\kappa$-opioid receptor (Pan Z. Z.: Trends Pharmacol Sci; 19,3: 94–8).

Opioids having selective or predominant $\kappa$-antagonist activity include, but are not limited to nalmefene, naltrexone, CHMMO, nor-binaltorphimine, (Portoghese, P. S., Lipkowski, A. W., Takemori, A. E.; Life Sciences 40: 1287–92); guanidylated naltrindole (GNTI), (Jones R. M., Hjorth, A. S., Schwartz, T. W., and Portoghese, P. S.; Journal of Medicinal Chemistry 41,25: 4911–4), (–)-(1R,5R,9R)-5, 9-diethyl-2-(3-furylmethyl)-2-hydroxy-6,7-benzomorphan (MR 2266) (Merz, H., Langbein, A., Stockhaus, K., Walther, G., & Wick, H.; Advances in biochemical psychopharmacology, Vol 8: 91–107), a triethylenedioxy derivative of naltrexamine (TENA), (Portoghese, P. S., Takemori, A. E.; Life Sciences 36: 801–5), buprenorphine, and diprenorphine, having essentially equal antagonist activity at the $\mu$ and $\kappa$ opioid receptors (Goodman and Gilman's The Pharmacologic Basis of Therapeutics, Chapter 23, p. 524).

Opioids having selective or predominant $\mu$-agonist activity include, but are not limited to, dihydromorphine, morphine, hydromorphone, methadone, fentanyl, sufentanyl, buprenorphine, demorphine, codeine, ethylinorphine, etonitazene, hydrocodone, levorphanol, norcodeine, normorphine, loperaniide, {D-Ala$^2$-N-Me-Phe$^4$-Gly$^5$-ol)-Enkephalin}(DAMGO), oxycodone and traniadol. Most opioids pass the Blood Brain Barrier (BBB) and are, therefore both, centrally and peripherally active, i.e. they can act upon CNS sites as well as peripheral sites, such as the gut and hormone producing glands, including the endocrine pancreas and the adrenal medulla. Some opioids, e.g. loperarnide, do not pass the BBB and are, therefore, only peripherally active with little or no CNS effect. Since drug addiction generally requires a central effect, peripherally acting opioid agonists are typically not addictive and generally not 'scheduled' as narcotics.

Buprenorphine is a mixed agonist-antagonist having high affinity at the $\mu$ opiate receptor with partial agonist activity, and at the $\kappa$ receptor with antagonist activity. Because of its $\kappa$ receptor antagonist activity and low partial $\mu$ activity it will produce minimal and perhaps clinically insignificant physical dependence. Buprenorphine has been used as an effective analgesic for the treatment of moderate to severe pain and of opioid dependence. (Lewis J. W.: Drug and Alcohol Dependence; 14:363–372). Elevations in cortisol and glucose, caused by surgical stress, have been observed to decline following the administration of buprenorphine to treat analgesia during and following total hip replacement (McQuay H. J. et. al.: Br J Anaesth; 52:1013–19).

Loperamide is a synthetic opioid used for the treatment of diarrhea, which is more effective and safe than other opioid drugs in the treatment of diarrhea of various causes (Ruppin H: Acta Physiol Scand; 127,3:275–9) Loperamide is a 'non-scheduled' opioid with $\mu$-agonist activity as opposed to most other opioid agonists which are listed as 'controlled substances.' Loperamide is reported to raise blood glucose concentrations at dose levels required for the acute treatment of diarrhea (Caldara R. et. al.: Eur J Clin Pharmacol; 21,3:185–8), and has been used in the "Loperamide test": a simple and highly specific screening test for hypercortisolism in children and adolescents" (Buzi F. et. al.: Acta Paediatr; 86,11: 1177–80).

The invention results in an improved method of treating coronary disease risk factors and an improvement toward normal values of fasting blood glucose, C-peptide, fasting total cholesterol, fasting LDL-cholesterol, fasting HDL-cholesterol, LDL/HDL ratio, fasting TG, fasting FFA, body weight, systolic blood pressure and/or diastolic blood pressure.

EXAMPLE

The example is being described for purely illustrative purposes, and is in no way meant to limit the scope of the invention.

The daily blood glucose profile of a 72 year old subject with Type 2 Diabetes and dyslipidemia was monitored following the early morning oral administration of 0.15 mg Hydrocodone, a centrally acting $\mu$-agonist in combination with sulfonylurea type insulin secretagogue. The glucose profile of the subject was monitored on the second day after the treatment had been initiated. Sufficient time was allowed after the earlier treatment to eliminate any carry-over effect.
Treatment 1
(-O-) no drug treatment.
Breakfast: 08:40–09:00; lunch: 12:25–12:50; dinner: 18:40–19:00

| time [h] | 08:10 | 10:00 | 12:20 | 14:00 | 18:30 | 20:00 |
|---|---|---|---|---|---|---|
| BG [mg/dL] | 132 | 156 | 104 | 150 | 98 | 117 |

Treatment 2

(-■-) 0.15 mg Hydrocodone, a centrally acting µ-agonist in combination with 1.0 mg Glipizide, administered 2 hours before breakfast.

Breakfast: 09:00–0915; lunch: 12:10–12:30; dinner: 19:20–19:50

| Time [h] | 08:45 | 09:00 | 09:15 | 09:50 | 10:35 | 11:05 | 12:10 | 12:30 | 13:00 | 14:05 | 19:25 | 19:50 | 20:25 | 20:55 |
|---|---|---|---|---|---|---|---|---|---|---|---|---|---|---|
| BG [mg/dL] | 103 | 102 | 102 | 108 | 116 | 104 | 109 | 100 | 108 | 94 | 92 | 88 | 105 | 89 |

FIG. 1 and the supporting data demonstrate that post prandial peaks in glucose concentration have been virtually normalized with the administration of 0.15 mg of hydrocodone in combination with 1.0 mg of the sulfonylurea type insulin secretagogue glipizide. The administration of the µ-agonist in combination with the insulin secretagogue also results in very significant increases in first phase insulin release, as can be derived from the pronounced decreases of blood glucose concentrations throughout the intake of the meals, and from the reduced duration and excursions of the post-prandial peaks, compared to placebo.

Type 2 Diabetes, IGT, overweight and obesity are associated with defective or lacking first phase insulin release, as is Type 1 Diabetes. In contrast to Type 1 Diabetes, all these afflictions, except late stage Type 2 Diabetes, retain second, proportional phase insulin secretory capacity. The restoration of hepatic carbohydrate oxidation and storage in Type 1 Diabetics requires appropriately controlled exogenous insulin infusions.

According to the present invention, such restoration of hepatic carbohydrate oxidation storage in subjects afflicted with the CHD risk factors is achieved by administration of opioidergic drug compositions in combination with insulin secretagogues. The opioidergic drug compositions useable in the present invention may be single substances or may also be any combination of opioid agonists, antagonists or mixed agonist/antagonists as long as their respective pharmacodynamics are, or have been rendered, compatible, in order to avoid significant variations in their respective, and combined, biologic effectiveness throughout their decline in biologic action.

The effective dose of the µ-agonist loperamide is, typically, less than 0.5 mg per day (or 7 µ/kg) or smaller by more than an order of magnitude than the typical dose required for the treatment of diarrhea, and the effective dose for hydrocodone is, typically, less than 1 mg (or 10 µ/kg). The effective dose for these and other p-agonists, or single- or multi-molecular mixed µ-agonistlic/κ-antagonist compositions as well as the insulin secretagogues may vary depending upon factors such as the (patho-)physiology of the subject being treated, receptor binding, the absorption rate, bio-availability, excretion rate and the rate of metabolism of the drug. The phannacokinetic compatibility between the opioidergic agent and the insulin secretagogue is less critical, but the preferred biologic half life of the insulin secretagogue is less than 4 hours. The preferred method of administration is such that the peak plasma concentration of the drug combination occurs before or during breakfast.

The effective dose for the supplementary insulin secretagogues is, typically, equal or less than the dose for such agents used in monotherapy.

The examples are being described for purely illustrative purposes, and are in no way meant to limit the scope of the invention.

I claim:

1. A method for treating one or more conditions of metabolic syndrome of Coronary Heart Disease Risk Factors (CHDRF) comprising at least one of Insulin Resistance, BetaCell Dysfunction, Impaired Glucose Tolerance, Type 2 Diabetes, overweightness, obesity and dyslipidemia in a patient suffering therefrom, the method comprising administering to said patient, by a pharmaceutically effective mode, a drug composition comprising:

an opioidergic agent; and an insulin secretagogue.

2. The method of claim 1, wherein the opioidergic agent is an opiate antagonist, an opiate having µ-agonist activity or a combination thereof.

3. The method of claim 2, wherein the opiate antagonist comprises a single molecular entity.

4. The method of claim 2, wherein the opiate antagonist comprises a combination of molecular entities.

5. The method of claim 2, wherein the opiate having µ-agonist activity comprises a single molecular entity.

6. The method of claim 2, wherein the opiate having µ-agonist activity comprises a combination of molecular entities.

7. The method of claim 2, wherein the drug composition comprises a peripherally acting µ-agonist.

8. The method of claim 7, wherein the drug composition comprises loperamide.

9. The method of claim 2, wherein the drug composition comprises a centrally acting µ-agonist.

10. The method of claim 2, wherein the drug composition further comprises an opiate having mixed µ-agonist and κ antagonist activity.

11. The method of claim 10, wherein the opiate having mixed µ-agonist and κ antagonist activity is buprenorphine.

12. The method of claim 2 wherein the opioidergic agent includes at least one of the following:

i) dihydromorphine;

ii) morphine;

iii) hydromorphone;

iv) methadone;

v) fentanyl;

vi) sufentanyl;

vii) buprenorphine;

viii) demorphine;

ix) codeine;

x) ethylmorphine;

xi) etonitazene;

xii) hydrocodone;

xiii) levorphanol;

xiv) norcodeine;

xv) normophine;

xvi) (D-Ala$^2$-N-Me-Phe$^4$-Gly$^3$-ol)-Enkephalin (DAMGO); and xvii) oxycodone.

13. The method of claim 2, wherein the opioidergic agent includes at least one of the following:

i) nalmefene;

ii) naltrexone;

iii) nor-binaltorphimine;

iv) (−)-(1R,5R,9R)-5,9-diethyl-2-(3-furylmethyl)-2-hydroxy-6,7-benzomorphan (MR 2266);

v) a triethylenedioxy derivative of B-naltrexamine (TENA); and vi) guanidylated naltrindole (GNTI).

14. The method of claim 2, wherein the condition included within the CHDRF Syndrome is Insulin Resistance (IR).

15. The method of claim 2, wherein the condition included within the CHDRF Syndrome is Beta-Cell Dysfunction.

16. The method of claim 2, wherein the condition included within the CHDRF Syndrome is Impaired Glucose Tolerance (IGT).

17. The method of claim 2, wherein the condition included within the CHDRF Syndrome is Type 2 Diabetes.

18. The method of claim 2, wherein the condition included within the CHDRF syndrome is overweight.

19. The method of claim 2, wherein the condition included within the CHDRF syndrome is obesity.

20. The method of claim 2, wherein the condition included within the CHDRF syndrome is dyslipidemia.

21. The method of claim 1, wherein the insulin secretagogue includes at least one of the following:

i. sulphonylureas;

ii. tolbutamide;

iii. chlorpropamide;

iv. glimepiride;

v. glipizide;

vi. glyburide;

vii. meglitinides;

viii. repaglinide;

ix. pramlintide;

x. morphilinoguanide;

xi. acetylcholine;

xii. muscannic agonists;

xiii. carbachol;

xiv. bethanechol;

xv. beta-L-glucose pentaacetate;

xvi. chiro-inositol;

xvii. myo-inositol;

xviii. GIP;

xix. GLP-1; and xx. Extendin-4.

22. The method of claim 1, wherein the insulin secretagogue is a non-glucose dependent insulin secretagogue, the method producing insulin release patterns capable of attaining glucose dependent, bi-phasic release characteristics with reduced likelihood of producing hypoglycemia.

23. The method of claim 22, wherein the insulin secretagogue is sulphonylurea.

24. A method for treating one or more conditions of metabolic syndrome of Coronary Heart Disease Risk Factors (CHDRF) comprising at least one of Insulin Resistance, BetaCell Dysfunction, Impaired Glucose Tolerance, Type 2 Diabetes, overweightness, obesity and dyslipidemia in a patient suffering therefrom, the method comprising administering to said patient, by a pharmaceutically effective mode, a drug composition comprising:

an opiate antagonist; and an insulin secretagogue.

25. The method of claim 24, wherein the opiate antagonist comprises a single molecular entity.

26. The method of claim 24, wherein the opiate antagonist comprises a combination of molecular entities.

27. The method of claim 24, wherein the opiate antagonist includes at least one of the following:

i) nalmefene ii) naltrexone;

iii) nor-binaltorphimine;

iv) (−)-(1R,5R,9R)-5,9-diethyl-2-(3-furylmethyl)-2-hydroxy-6,7-benzomorphan (MR 2266);

v) a triethylenedioxy derivative of B-naltrexamine (TENA); and vi) guanidylated naltrindole (GNTI).

28. The method of claim 24, wherein the condition included within the CHDRF Syndrome is Insulin Resistance.

29. The method of claim 24, wherein the condition included within the CHDRF Syndrome is Beta-Cell Dysfunction.

30. The method of claim 24, wherein the condition included within the CHDRF syndrome is Impaired Glucose Tolerance (IGT).

31. The method of claim 24, wherein the condition included within the CHDRF syndrome is Type 2 Diabetes.

32. The method of claim 24, wherein the condition included within the CHDRF syndrome is overweight.

33. The method of claim 24, wherein the condition included within the CHDRF syndrome is obesity.

34. The method of claim 24, wherein the condition included within the CHDRF syndrome is dyslipidemia.

35. The method of claim 24 wherein the opiate antagonist has IC$_{50}$ levels for the $\mu$, $\delta$, and $\kappa$ opiate receptors, the IC$_{50}$ levels being $\{(IC_{50}\kappa/IC_{50}\mu)<3\}$ and $\{(IC_{50}\kappa/IC_{50}\delta)<3\}$.

36. The method of claim 24, wherein the insulin secretagogue includes at least one of the following:

i. sulphonylureas;

ii. tolbutamide;

iii. chlorpropamide;

iv. glimepiride;

v. glipizide;

vi. glyburide;

vii. meglitinides;

viii. repaglinide;

ix. pramlintide;

x. morphilinoguanide;

xi. acetylcholine;

xii. muscannic agonists;

xiii. carbachol;

xiv. bethanechol;

xv. beta-L-glucose pentaacetate;

xvi. chiro-inositol;

xvii. myo-inositol;

xviii. GIP;

xix. GLP-1; and xx. Extendin-4.

37. The method of claims 24, wherein the insulin secretagogue is a non-glucose dependent insulin secretagogue, the method producing insulin release patterns capable of attaining glucose dependent, bi-phasic release characteristics with reduced likelihood of producing hypoglycemia.

38. The method of claim 37, wherein the insulin secretagogue is sulphonylurea.

39. A method for treating one or more conditions of metabolic syndrome of Coronary Heart Disease Risk Factors (CHDRF) comprising at least one of Insulin Resistance, BetaCell Dysfunction, Impaired Glucose Tolerance, Type 2 Diabetes, overweightness, obesity and dyslipidemia in a patient suffering therefrom, the method comprising administering to said patient, by a pharmaceutically effective mode, a drug composition comprising:

an opiate agonist; and an insulin secretagogue.

40. The method of claim 39, wherein the opiate agonist comprises a single molecular entity.

41. The method of claim 39, wherein the opiate agonist comprises a combination of molecular entities.

42. The method of claim 39, wherein the opiate agonist is a peripherally acting $\mu$-agonist.

43. The method of claim 42, wherein the opiate agonist is loperamide.

44. The method of claim 39, wherein the opiate agonist is a centrally acting $\mu$agonist.

45. The method of claim 39, wherein the opiate agonist includes at least one of the following:

i) dihydromorphine;

ii) morphine;

iii) hydromorphone;

iv) methadone;

v) fentanyl;

vi) sufentanyl;

vii) demorphine;

viii) codeine;

ix) ethylmorphine;

x) etonitazene;

xi) hydrocodone;

xii) levorphanol;

xiii) norcodeine;

xiv) normophine;

xv) (D-Ala$^2$-N-Me-Phe$^4$-Gly$^3$-ol)-Enkephalin (DAMGO); and xvi) oxycodone.

46. The method of claim 39, wherein the condition included within the CHDRF Syndrome is Insulin Resistance.

47. The method of claim 39, wherein the condition included within the CHDRF Syndrome is Beta-Cell Dysfunction.

48. The method of claim 39, wherein the condition included within the CHDRF syndrome is Impaired Glucose Tolerance (IGT).

49. The method of claim 39, wherein the condition included within the CHDRF syndrome is Type 2 Diabetes.

50. The method of claim 39, wherein the condition included within the CHDRF syndrome is overweight.

51. The method of claim 39, wherein the condition included within the CHDRF syndrome is obesity.

52. The method of claim 39, wherein the condition included within the CHDRF syndrome is dyslipidemia.

53. The method of claim 39, wherein the insulin secretagogue includes at least one of the following:

i. suipnonylureas;

ii. tolbutamide;

iii. chlorpropamide;

iv. glimepiride;

v. glipizide;

vi. glyburide;

vii. meglitinides;

viii. repaglinide;

ix. pramlintide;

x. morphilinoguanide;

xi. acetylcholine;

xii. muscarimc agonists;

xiii. carbachol;

xiv. bethanechol;

xv. beta-L-glucose pentaacetate;

xvi. chiro-inositol;

xvii. myo-inositol;

xviii. GIP;

xix. GLP-1; and xx. Extendin-4.

54. The method of claims 39, wherein the insulin secretagogue is a non-glucose dependent insulin secretagogue, the method producing insulin release patterns capable of attaining glucose dependent, bi-phasic release characteristics with reduced likelihood of producing hypoglycemia.

55. The method of claim 39, wherein the insulin secretagogue is sulphonylurea.

56. The method of claim 2, wherein opiate agonist comprises tramadol.

57. The method of claim 2, wherein the drug composition comprises at least one of CHMMO, diprenorphine, and a combination thereof.

58. The method of claim 2, wherein the opiate antagonist has $IC_{50}$ levels for the $\mu$, $\delta$, and $\kappa$ opiate receptors, the $IC_{50}$ levels being $\{(IC_{50}\kappa/IC_{50}\mu)<3\}$ and $\{(IC_{50}\kappa/IC_{50}\delta)<3\}$.

59. The method of claim 2, wherein the opiate antagonist has $IC_{50}$ levels for the $\mu$, $\delta$, and $\kappa$ opiate receptors, the $IC_{50}$ levels being $\{(IC_{50}\kappa/IC_{50}\mu)<10\}$ and $\{(IC_{50}\kappa/IC_{50}\delta)<10\}$.

60. The method of claim 1, wherein the drug composition is administered in a daily dose comprising less than about 10 $\mu$g/kg opioidergic agent and equal to or less than about 10 $\mu$g/kg of insulin secretagogue for monotherapy.

61. The method of claim 39, wherein opiate agonist comprises tramadol.

62. The method of claim 24, wherein the drug composition comprises at least one of CHMMO, diprenorphine, and a combination thereof.

63. The method of claim 24, wherein the opiate antagonist has $IC_{50}$ levels for the $\mu$, $\delta$, and $\kappa$ opiate receptors, the $IC_{50}$ levels being $\{(IC_{50}\kappa/IC_{50}\mu)<10\}$ and $\{(IC_{50}\kappa/IC_{50}\delta)<10\}$.

* * * * *